United States Patent [19]

Chaikin

[11] 4,180,872
[45] Jan. 1, 1980

[54] WATERPROOF PROSTHETIC FOOT AND METHOD OF MAKING SAME

[76] Inventor: Neal S. Chaikin, 4505 Hornbeam Dr., Rockville, Md. 20853

[21] Appl. No.: 855,370

[22] Filed: Nov. 28, 1977

[51] Int. Cl.² .............................................. A61F 1/08
[52] U.S. Cl. ...................................... 3/7; 12/142 EV; 36/4; 36/7.3; 156/280
[58] Field of Search .................. 3/6, 6.1, 7, 5; 36/7.3, 36/7.4, 4, 8.1, 110; 12/142 E, 142 EV, 142 F; 156/280

[56] References Cited

U.S. PATENT DOCUMENTS

| 166,669 | 8/1875 | Williams | 36/7.3 X |
|---|---|---|---|
| 470,431 | 3/1892 | Marks | 3/7 X |
| 1,032,074 | 7/1912 | Marks | 3/7 X |
| 1,150,702 | 8/1915 | Pierce | 36/8.1 |
| 1,812,156 | 6/1931 | Leaf | 3/7 |
| 1,972,976 | 9/1934 | Bunham et al. | 36/4 X |
| 1,977,576 | 10/1934 | Dunker | 12/142 E |
| 2,103,511 | 12/1937 | Brown | 3/6 |
| 2,426,211 | 8/1947 | Heckman | 36/4 |
| 2,789,933 | 4/1957 | Bargmeyer | 36/7.3 X |
| 3,400,408 | 9/1968 | Garcia | 3/7 X |

FOREIGN PATENT DOCUMENTS 364958 1/1932 United Kingdom .......................... 36/4
381347 7/1973 U.S.S.R. .......................................... 3/6

Primary Examiner—Clifford D. Crowder
Attorney, Agent, or Firm—Robert H. Epstein

[57] ABSTRACT

An improvement for waterproofing a prosthetic foot of the type having a foot body surrounding a keel includes a layer of water repellent resilient material cemented to a bottom surface and front, rear and side edges of a lower portion of the foot body extending from the toe to the heel and a coating of water repellent material covering the top portion of the foot body and the interface of the edges of the layer of water repellent resilient material with the lower portion of the foot body such that the prosthetic foot can be immersed in water while the water is prevented from reaching the keel. A method of waterproofing a prosthetic foot includes the steps of cementing a substantially flat sole made of water repellent resilient material to the bottom surface of the foot body with a waterproof sealing adhesive, cementing a band of water repellent resilient material to the sole extending substantially transversely therefrom and to the front, rear and side edges of the lower portion of the foot body and coating the foot body with the water repellent material to cover the upper portion of the foot body and the interface of the edges of the band with the lower portion of the foot body.

6 Claims, 5 Drawing Figures

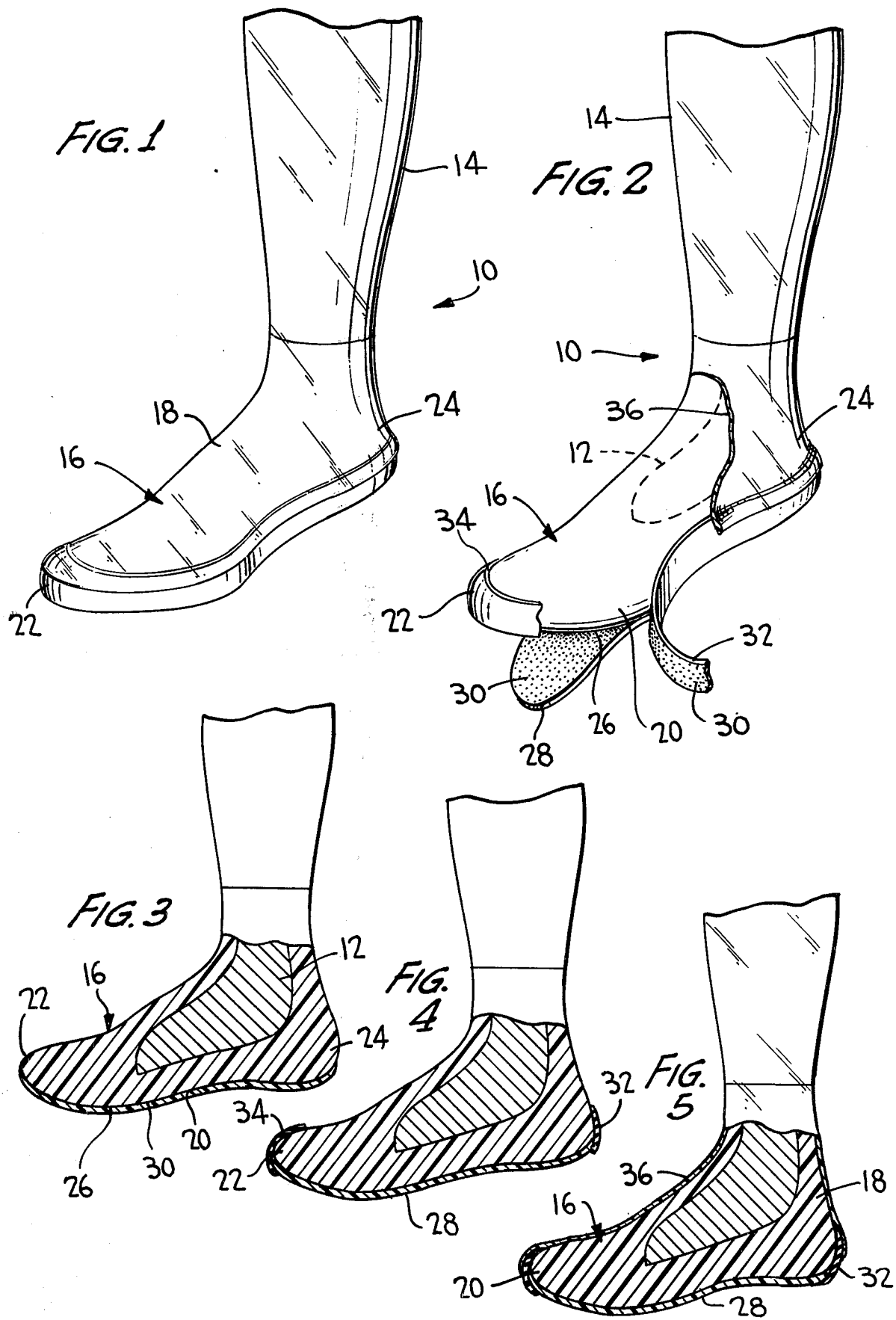

WATERPROOF PROSTHETIC FOOT AND METHOD OF MAKING SAME

BACKGROUND OF THE INVENTION

1. Field of the Invention

The present invention pertains to prosthetic devices and, more particularly, to an improvement for waterproofing a prosthetic foot.

2. Discussion of the Prior Art

Many people must utilize prosthetic feet in order to perform normal daily tasks; however, while prosthetic feet have been improved in order to facilitate walking, running and other physical activities, no prosthetic foot has been developed to date which will permit a wearer to immerse the foot in water, such as while showering, bathing or swimming. When a conventional prosthetic foot is immersed in water, the water will seep into the interface between the wood block, called the keel, and the foot body molded around the keel, such seepage causing warping of the keel and rendering the prosthetic foot defective for normal use. Accordingly, it has been the practice in the past for a wearer of a prosthetic foot to remove the foot prior to engaging in any activity where the foot would be exposed to water. Removal of the prosthetic foot has the disadvantages of being time consuming, presenting a disconcerting appearance and causing a situation where the person must awkwardly transport himself from a swimming pool, beach or the like without the use of the prosthetic foot. Normally, a person utilizing a prosthetic foot also requires an artificial leg; and, thus, the problem of transporting oneself becomes increasingly difficult.

There have been attempts in the past to waterproof prosthetic feet, as exemplified by U.S. Pat. No. 1,812,156 to Leaf, U.S. Pat. No. 2,103,511 to Brown, and U.S. Pat. No. 2,451,980 to Samons, Sr. and Russian Pat. No. 381,347; however, prior attempts have suffered the disadvantages of not being useable with conventional prosthetic foot structures, of rendering the prosthetic foot stiff and difficult to utilize for normal activities and/or of being relatively fragile and requiring continued inspection and maintenance when used on hard and abrasive surfaces.

SUMMARY OF THE INVENTION

Accordingly, it is a primary object of the present invention to overcome the above-mentioned disadvantages of the prior art by providing an improvement for waterproofing a conventional prosthetic foot while permitting the prosthetic foot to remain flexible and not requiring a change in structure of the prosthetic foot.

Another object of the present invention is to secure a layer of water repellent resilient material to a prosthetic foot to withstand continued use directly on abrasive surfaces while maintaining the prosthetic foot in a watertight condition.

A further object of the present invention is to cement a layer of water repellent resilient material to the lower portion of a foot body of a prosthetic foot and coat an upper portion of the foot body with a water repellent material to cover the interface of the layer of water repellent resilient material with the foot body, the layer of water repellent material and the coating material being resilient to permit the prosthetic foot to retain normal flexibility.

The present invention has a further object in that conventional, commercially available prosthetic feet can be waterproofed without altering the structure or characteristics of the feet.

Some of the advantages of the present invention over the prior art are that the method of waterproofing a prosthetic foot according to the present invention is simple and inexpensive to implement while being extremely effective and long lasting, and the waterproofing materials can be simply and inexpensively replaced should they be worn from use.

The present invention is generally characterized in an improvement for waterproofing a prosthetic foot formed of a keel adapted to be coupled with a lower end of an artificial leg portion and a foot body surrounding the keel and having an upper portion and a lower portion defining a toe, a heel and a bottom surface extending from the toe to the keel, the improvement including a layer of water repellent resilient material secured to the bottom surface of the foot body extending from the toe to the heel, and a coating of water repellent material covering the top portion of the foot body and the interface of the edges of the layer of water repellent resilient material with the foot body whereby the prosthetic foot can be immersed in water while water is prevented from reaching the keel.

The present invention is further generally characterized in a method of waterproofing a prosthetic foot of the type having a keel and a foot body surrounding the keel and having an upper portion and a lower portion defining a toe, a heel and a bottom surface extending from the toe to the heel including the steps of cementing a layer of water repellent resilient material to the lower portion of the foot body with a waterproof sealing adhesive, and coating the foot body with a water repellent material to cover the upper portion of the foot body and the interface of the edges of the layer of water repellent resilient material with the lower portion of the foot body.

Other objects and advantages of the present invention will become apparent from the following description of the preferred embodiment taken in conjunction with the accompanying drawings.

BRIEF DESCRIPTION OF THE DRAWINGS

FIG. 1 is a perspective view of an improved waterproof prosthetic foot according to the present invention.

FIG. 2 is a perspective view of the improved waterproof prosthetic foot of FIG. 1 with parts broken away.

FIGS. 3, 4 and 5 are cross-sectional views illustrating a method of waterproofing a prosthetic foot according to the present invention.

DESCRIPTION OF THE PREFERRED EMBODIMENT

A waterproof prosthetic foot 10 according to the present invention is illustrated in FIGS. 1 and 2 and includes a block of wood forming a keel 12 adapted to be coupled with a lower end of an artificial leg 14 via any conventional coupling, such as a ball and socket joint or the like, and a foot body generally indicated at 16 having an upper portion 18 and a lower portion 20 defining a toe 22, a heel 24 and a bottom surface 26 extending from the toe to the heel. The prosthetic foot, as thus far described, is conventional; and, thus, no additional detailed description thereof is set forth, it being noted that the foot body 16 is normally formed of a soft resilient material, such as polyurethane resin, molded around the keel 12 such that the toe and ball of the foot body present a flexibility similar to that of walking on a normal foot.

In accordance with the present invention, a substantially flat sole 28 of water repellent resilient material is cemented to the bottom surface 26 of the foot body with a waterproof sealing adhesive 30, and a strip or band of water repellent resilient material 32 extends substantially transversely from the edges of the sole 28 and is cemented to the front, rear and side edges of the foot body and to the edges of the sole 28 by means of the waterproof sealing adhesive 30. If desired for situations where the prosthetic foot 10 is subjected to overly abrasive conditions, such as walking in sand, the band of material 32 can have an overlapping portion 34 extending inwardly over the toe, heel and sides of the lower portion 20 of the foot body. A coating 36 of water repellent material, such as silicone rubber, covers the upper portion 18 of the foot body 16 and the interface of the lower portion foot body with the band of material 32.

Preferably, the sole 28 and band 32 are made of the same material which should be wear-resistant as well as water repellent. Examples of materials which are suitable for such purposes are natural or synthetic rubber, such as butyl rubber, styrene-butadiene copolymers and polyene rubbers, such as polybutadiene and neoprene. The adhesive 30 can be any waterproof, sealing cement, such as Barge All-Purpose Cement.

A method of waterproofing to form the prosthetic foot of FIGS. 1 and 2 is illustrated in FIGS. 3, 4 and 5 and includes initially the step of cementing the sole 28 to the bottom surface 26 of the foot body 16 with cement 30, the sole 28 extending from toe 22 to heel 24. Thereafter, the band of material 32 is cemented in place with its lower edge overlapping the side edge of the sole and the wider portion 34 extending over the toe 22, as shown in FIG. 4. Once the sole 28 and band 32 are cemented in place, the foot is coated with silicone rubber 36, as shown in FIG. 5, to cover the upper portion 18 of the foot body and the interface of the upper edges of the band 32 with the lower portion of the foot body.

If desired, the sole 28 and the band 32 can be stapled in place to add structural stability to the sealing characteristics of the adhesive 30. Additionally, the sole 28 and the band 32 could be integrally formed of a single piece of water repellent resilient material if desired.

Inasmuch as the present invention is subject to many variations, modifications and changes in detail, it is intended that all subject matter discussed above or shown in the accompanying drawings be interpreted as illustrative and not in a limiting sense.

What is claimed is:

1. An improvement for waterproofing a prosthetic foot formed of a keel adapted to be coupled with a lower end of an artificial leg and a foot body surrounding the keel and having an upper portion and a lower portion defining a toe, a heel and a bottom surface extending from said toe to said heel and front, rear and side surfaces extending upward to the upper portion from the toe, the heel and the sides of the bottom surface, respectively, said improvement comprising
   a substantially flat sole of water repellent resilient material secured to the bottom surface of the foot and extending from the toe to the heel;
   a band of water repellent resilient material secured to the front, rear and side surfaces of the lower portion of the foot body to overlap the edge of said sole and extend substantially transversely therefrom;
   water repellent cement adhesively securing said sole and said band to said foot body; and
   a coating of water repellent material covering the top portion of the foot body and the interface of the edges of said band of water repellent resilient material with the foot body whereby the prosthetic foot can be immersed in water while water is prevented from reaching the keel.

2. An improvement for waterproofing a prosthetic foot as recited in claim 1 wherein said band of water repellent resilient material has a top edge extending inwardly over the toe of the foot body.

3. An improvement for waterproofing a prosthetic foot as recited in claim 2 wherein said band of water repellent resilient material extends over the heel and sides of the lower portion of the foot body.

4. An improvement for waterproofing a prosthetic foot as recited in claim 1 wherein said water repellent resilient material is rubber and said coating of water repellent material is silicone rubber.

5. A method of waterproofing a prosthetic foot of the type having a keel and a foot body surrounding the keel and having an upper portion and a lower portion defining a toe, a heel and a bottom surface extending from the toe to the heel comprising the steps of
   cementing a substantially flat sole made of water repellent resilient material to the bottom surface of the foot body with a waterproof sealing adhesive;
   cementing a band of water repellent resilient material to the front, rear and side edges of the lower portion of the foot body, the band extending substantially transversely from the sole and overlapping the edge thereof; and
   coating the foot body with a water repellent material to cover the upper portion of the foot body and the interface of the edges of the band of water repellent resilient material with the lower portion of the foot body.

6. A method as recited in claim 5 wherein the sole and band are made of rubber and the coating material is silicone rubber.

* * * * *